US00PP20980P2

(12) United States Plant Patent
Egger

(10) Patent No.: US PP20,980 P2
(45) Date of Patent: May 4, 2010

(54) ***AGASTACHE* PLANT NAMED 'SUMMER GLOW'**

(50) Latin Name: ***Agastache* hybrid**
Varietal Denomination: Summer Glow

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/383,648

(22) Filed: Mar. 27, 2009

(51) Int. Cl.
*A01H 5/00* (2006.01)

(52) U.S. Cl. ..... Plt./399

(58) Field of Classification Search ..... Plt./399
See application file for complete search history.

*Primary Examiner*—Kent L Bell
(74) *Attorney, Agent, or Firm*—Klarquist Sparkman, LLP

(57) ABSTRACT

A new and distinct form of *Agastache* plant characterized by light orange yellow flowers, dark calyces, an upright branching habit, a long bloom time, and excellent vigor.

1 Drawing Sheet

Botanical denomination: *Agastache* hybrid.
Variety designation: 'Summer Glow'.
Parentage: *Agastache* sp. 'Pink Pop'×*Agastache aurantiaca* 'Apricot Sunrise'.

BACKGROUND OF THE INVENTION

The present invention relates to a new and distinct cultivar of *Agastache,* given the name, 'Summer Glow'. *Agastache* is in the family Lamiaceae. This new variety is from a cross between a dwarf form of *Agastache* sp. 'Pink Pop' (an unpatented plant) as the seed parent and *Agastache aurantiaca* 'Apricot Sunrise' (unpatented) as the pollen parent. Compared to the seed parent, *Agastache* sp. 'Pink Pop', the new cultivar has light orange yellow flowers rather than pink. Compared to the pollen parent, *Agastache aurantiaca* 'Apricot Sunrise', the new cultivar has light orange yellow flowers rather than orange.

This plant exhibits the following characteristics that make it unique:

1. light orange yellow flowers,
2. dark calyces,
3. an upright branching habit,
4. a long bloom time, and
5. excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a nine-month-old *Agastache* 'Summer Glow' growing in the field in late summer in Canby, Oreg.

DETAILED PLANT DESCRIPTION

The following is a detailed description of the new *Agastache* cultivar based on observations of a nine-month-old specimen grown in the greenhouse then planted outside in the ground in May in the trial beds in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Upright.
*Type.*—Herbaceous perennial.
*Cold hardiness.*—USDA Zone 7–10 .
*Size.*—Grows to 42 cm wide and 63 cm tall to the top of the flowers.
*Vigor.*—Excellent.
*Stem.*—Square in cross section, grows to 4 mm wide and 63 cm tall, sparsely pubescent, internodes range from 2 cm to 8 cm long, Yellow Green 147B.
*Roots.*—White 155B, fibrous, plants root easily from stem tip cuttings.

Leaf:

*Type.*—Simple.
*Arrangement.*—Opposite.
*Shape.*—Ovate.
*Venation.*—Pinnate.
*Margins.*—Crenate.
*Apex.*—Acute.
*Base.*—Truncate.
*Blade size.*—Grows to 40 mm long and 25 mm wide.
*Surface texture.*—Very short hairs on both sides.
*Petiole description.*—12 mm long and 1 mm wide, pubescent, Yellow Green 147B.
*Leaf color.*—Top side closest to Green 147A, bottom side closest to Yellow Green 147B.

Inflorescence:

*Type.*—Terminal spike with 7 to 14 whorls.
*Number of flowers.*—Up to 220 per spike.
*Size of inflorescence.*—9 cm to 39 cm tall and 5 cm wide.
*Peduncle.*—7 cm to 39 cm tall and 3 mm wide, pubescent, Yellow Green 147B.
*Pedicel.*—2 mm to 3 mm long, pubescent, Yellow. Green 147B.
*Bloom period.*—June through frost in Canby, Oreg.

Flower bud:

*Size.*—15 mm long and 3 mm wide at the widest point prior to opening.

*Description.*—Tubular.

*Surface texture.*—Pubescent.

*Color.*—Yellow Orange 22A.

Flower:

*Type.*—Zygomorphic.

*Shape.*—Bilabiate, tubular.

*Size.*—29 mm long and 10 mm wide.

*Corolla description.*—29 mm long and spreads to 10 mm wide; color inside and out Yellow Orange 15D darkening to Greyed Orange 174A under the calyx; pubescent outside and glabrous inside, tube 22 mm long and 1 mm to 4 mm wide; 2 upper lobes joined 3 mm long and 4 mm wide, ovate, acute, entire; three lower lobes, two spreading sideways and curve down slightly, each 2.5 mm long and 2.5 mm wide, acute, entire; the bottom lobe broad, reflexed, obovate, notched at the tip, entire, 5.5 mm wide and 5 mm deep.

*Calyx description.*—7 mm long and 2.5 mm wide, pubescent outside and glabrous inside, 5 lobed, lobes narrow, 2 mm long, entire, acuminate, color between Greyed Purple 187B and Grey 201A.

*Pistil description.*—21 mm long, ovary 0.5 mm long, Yellow Green 146C, style 19.5 mm long, Yellow 16D; stigma two-parted, 1 mm, Greyed Purple 187B.

*Stamen description.*—4 in number, paired with top two exerted and 9 mm long and bottom two 7 mm long, filaments Yellow 16D, anthers 0.5 mm long, Brown 200B, pollen White 155A.

*Fragrance.*—Light herbal.

*Lastingness.*—A spike blooms for about 3 weeks on the plant.

Fruit/seed: 4 nutlets, 1 mm long, ovoid, Black 202A.

Pests and diseases: *Agastache* are known to be susceptible to mildew and rust in dry summer months. The new cultivar has no known resistances but has shown no problems in Canby, Oreg.

I claim:

1. A new and distinct cultivar of *Agastache* plant substantially as shown and described.

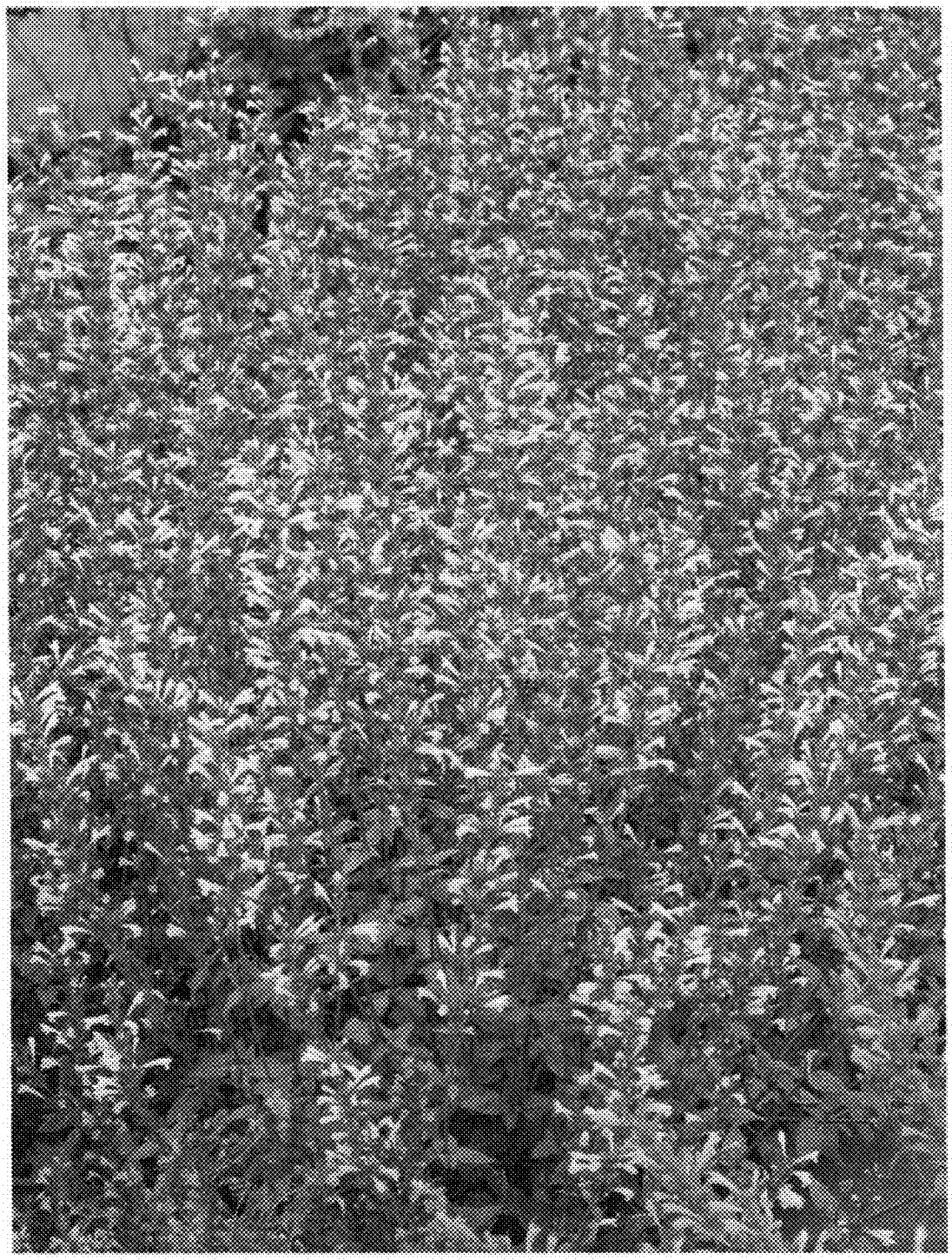

* * * * *